(12) United States Patent
Katsuhara et al.

(10) Patent No.: US 7,919,657 B2
(45) Date of Patent: Apr. 5, 2011

(54) PROCESS FOR DEHYDRATION OF HEXAFLUOROACETONE HYDRATE

(75) Inventors: Yutaka Katsuhara, Kawagoe (JP); Tatsuya Hayasaka, Iruma-gun (JP); Yoshiaki Miyamoto, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 12/675,725

(22) PCT Filed: Aug. 28, 2008

(86) PCT No.: PCT/JP2008/065359
§ 371 (c)(1), (2), (4) Date: Feb. 26, 2010

(87) PCT Pub. No.: WO2009/028584
PCT Pub. Date: Mar. 5, 2009

(65) Prior Publication Data
US 2010/0217049 A1  Aug. 26, 2010

(30) Foreign Application Priority Data

Aug. 29, 2007  (JP) ................................. 2007-222846

(51) Int. Cl.
*C07C 45/66* (2006.01)
(52) U.S. Cl. ...................................... 568/394; 568/411
(58) Field of Classification Search ................... 568/394, 568/411
See application file for complete search history.

(56) References Cited

U.S. PATENT DOCUMENTS

| 4,386,223 A | 5/1983 | Kawai et al. |
| 4,544,772 A | 10/1985 | Sawai et al. |
| 4,579,974 A | 4/1986 | Cheminal et al. |

FOREIGN PATENT DOCUMENTS

| JP | 44-9654 B1 | 5/1969 |
| JP | 46-6761 B1 | 2/1971 |
| JP | 53-71006 A | 6/1978 |
| JP | 57-81433 | 5/1982 |
| JP | 59-157045 | 9/1984 |
| JP | 59-204149 A | 11/1984 |
| JP | 60-185742 A | 9/1985 |

OTHER PUBLICATIONS

Knunyants et al., Fluorinated Compounds. Institute of Heteroorganic Compounds, Academy of Sciences of the USSR. No. 4, pp. 686-692, 1960. Translated from Izvestiya Akademil Nauk SSR, Otdelenie Khimicheskikh Nauk, translated pp. 647-653.
International Search Report mailed Sep. 22, 2008 with English translation, PCT/ISA/210. Five (5) pages.
Written Opinion of the International Searching Authority, PCT/ISA/237. Three (3) pages.

*Primary Examiner* — Sikarl A Witherspoon
(74) *Attorney, Agent, or Firm* — Crowell & Moring LLP

(57) ABSTRACT

To provide a process for producing anhydrous hexafluoroacetone from hexafluoroacetone hydrate. To provide a process taking environment into consideration, that does not require a treatment of wastes, such as waste sulfuric acid, containing organic substances, which is inevitable in processes conducted hitherto using concentrated sulfuric acid, fuming sulfuric acid, and the like.

A process for dehydrating a hexafluoroacetone hydrate, comprising introducing a hexafluoroacetone hydrate and hydrogen fluoride either as a mixture or separately into a distillation column, obtaining a composition containing hexafluoroacetone or a hexafluoroacetone-hydrogen fluoride adduct and hydrogen fluoride as a low boiling component, and obtaining a composition containing water and hydrogen fluoride as a high boiling component.

19 Claims, No Drawings

PROCESS FOR DEHYDRATION OF HEXAFLUOROACETONE HYDRATE

TECHNICAL FIELD

The present invention relates to a process for dehydrating a hexafluoroacetone hydrate by hydrogen fluoride, and furthermore relates to a process for producing a hexafluoroacetone-hydrogen fluoride adduct.

BACKGROUND TECHNIQUE

Hexafluoroacetone is produced in a large amount as an industrial raw material of 2,2-bis(4-hydroxyphenyl)hexafluoropropane (bisphenol-AF), which is important as a crosslinking agent of fluororubber, hexafluoroisopropanol, which is important as a medicine intermediate, and the like. Industrially, hexafluoroacetone is produced by a process by an epoxidation of hexafluoropropene and a subsequent isomerization, a process by subjecting hexachloroacetone obtained by chlorinating acetone to a substitution fluorination with hydrogen fluoride by a chromium-supported activated carbon catalyst or the like, etc. Hexafluoroacetone is a gas having a boiling point of −28° C. under atmospheric pressure. Therefore, in order to meet the convenience of handling, hexafluoroacetone trihydrate, which is obtained as a constant boiling composition of 106° C., is used as a raw material in many reactions or served for storage. There are, however, some cases in which existence of water is not permissible depending on the reaction conditions, the target product and other requirements. Furthermore, hydrates are generally lower in reactivity in many cases, as compared with anhydrides. Therefore, anhydride of hexafluoroacetone is requested in some cases, and upon use it is frequently conducted to convert the hydrate to the anhydride in place.

As a process for dehydrating a hexafluoroacetone hydrate, there have been reported processes by the contact with Molecular Sieve (a registered trade mark) (Patent Publication 1), concentrated sulfuric acid, sulfuric anhydride, phosphorus pentoxide (Patent Publication 2), etc. By using concentrated sulfuric acid, sulfuric anhydride, phosphorus pentoxide, fuming sulfuric acid or the like as the dehydrator, hexafluoroacetone decomposition products may be produced. Furthermore, there occurs a waste in a large amount of sulfuric acid or phosphoric acid containing water and organic matters produced by the decomposition. Furthermore, there is also a problem that recovery percentage of hexafluoroacetone is not necessarily high when the dehydration is conducted by these processes including the case of using a synthetic zeolite.

On the other hand, hydrogen fluoride may be used as a catalyst or solvent in reactions using hexafluoroacetone as a raw material. For example, bisphenol-AF is obtained by a dehydration reaction from a mixture of hexafluoroacetone, phenol and hydrogen fluoride (Non-patent Publication 1).

Patent Publication 1: Japanese Patent Application Publication 59-157045
Patent Publication 2: Japanese Patent Application Publication 57-81433
Non-patent Publication 1: Isz. Akad-Nauk SSSR, Otdel. Khim, Nauk, vol. 4 pp. 686-692 (1960); English version pp. 647-653

DISCLOSURE OF THE INVENTION

Task to be Solved by the Invention

There is provided a process of obtaining a mixture of a hexafluoroacetone-hydrogen fluoride adduct and hydrogen fluoride by dehydrating a hexafluoroacetone hydrate, the process generating substantially no waste.

Means for Solving Task

As a result of a study about a process for industrially producing a hexafluoroacetone-hydrogen fluoride adduct, which shows a reaction behavior similar to that of hexafluoroacetone in specific reactions, the present inventors have found that a hydrogen fluoride solution of a hexafluoroacetone-hydrogen fluoride adduct can quantitatively be produced with good yield and substantially no generation of waste through dehydration of a hexafluoroacetone hydrate by a simple process comprising mixing a hexafluoroacetone hydrate with hydrogen fluoride and then conducting distillation, thereby completing the present invention.

That is, the present invention is a process for producing a hexafluoroacetone-hydrogen fluoride adduct, comprising separately obtaining a component containing a hexafluoroacetone-hydrogen fluoride adduct and hydrogen fluoride and a component containing water and hydrogen fluoride by bringing a hexafluoroacetone hydrate into contact with hydrogen fluoride and conducting distillation as it is.

Aspects 1-5 of the present invention are shown in the following.

Aspect 1 of the present invention is a process for dehydrating a hexafluoroacetone hydrate, comprising introducing a hexafluoroacetone hydrate and hydrogen fluoride either as a mixture or separately into a distillation column, obtaining a composition containing hexafluoroacetone or a hexafluoroacetone-hydrogen fluoride adduct and hydrogen fluoride as a low boiling component, and obtaining a composition containing water and hydrogen fluoride as a high boiling component.

Aspect 2 of the present invention is a dehydration process according to Aspect 1, wherein the hexafluoroacetone hydrate and the hydrogen fluoride are continuously introduced either as a mixture or separately into the distillation column.

Aspect 3 of the present invention is a process for dehydrating a hexafluoroacetone hydrate, comprising continuously introducing a hexafluoroacetone hydrate and hydrogen fluoride either as a mixture or separately into a distillation column, continuously obtaining a composition containing hexafluoroacetone or a hexafluoroacetone-hydrogen fluoride adduct and hydrogen fluoride as a low boiling component from a column top portion, and continuously obtaining a composition containing water and hydrogen fluoride as a high boiling component from a column bottom portion.

A dehydration process according to any of claims 1-3, wherein the hexafluoroacetone hydrate is hexafluoroacetone trihydrate.

Aspect 4 of the present invention is a dehydration process according to any of Aspects 1-3, wherein the hexafluoroacetone hydrate is hexafluoroacetone trihydrate.

Aspect 5 of the present invention is a dehydration process according to any of Aspects 1-4, wherein the hexafluoroacetone hydrate is a hexafluoroacetone hydrate containing water.

ADVANTAGEOUS EFFECT OF THE INVENTION

In the dehydration process of the present invention, since hexafluoroacetone or a hexafluoroacetone-hydrogen fluoride adduct to be obtained is in a mixture with hydrogen fluoride, it can be used as it is for a reaction in which hexafluoroacetone is used with hydrogen fluoride as a raw material, catalyst or solvent. Therefore, it is effective for simplification of the steps. Furthermore, it is a superior process on the side of environmental protection too, since it does not require a treatment of waste such as waste sulfuric acid containing organic materials, which is inevitable in processes conducted hitherto using concentrated sulfuric acid, fuming sulfuric acid, and the like.

BEST MODE FOR CARRYING OUT THE INVENTION

In the following, the present invention is explained in detail.
In the description, hydrogen fluoride may be represented by HF.
In the description, hexafluoroacetone may be represented by HFA.
In the description, a hexafluoroacetone-hydrogen fluoride adduct may be represented by HFA-HF.
In the description, a hexafluroacetone hydrate refers to a hydrate or its aqueous solution with unlimited hydration number and is a concept containing hexafluoroacetone trihydrate.
In the description, hexafluoroacetone trihydrate may be represented by HFA-3W.

The present invention is a process for producing a hexafluoroacetone-hydrogen fluoride adduct, comprising separately obtaining a component containing a hexafluoroacetone-hydrogen fluoride adduct and hydrogen fluoride and a component containing water and hydrogen fluoride by bringing a hexafluoroacetone hydrate into contact with hydrogen fluoride and conducting distillation as it is. Here, "as it is" refers to without conducting a treatment by a chemical substance that is used generally as a dehydrator, such as concentrated sulfuric acid, sulfuric anhydride, phosphorus pentoxide, and the like, or by an adsorbent such as molecular sieves and the like. However, not "as it is", that is, it is natural to be able to conduct a dehydration by these dehydrators before or after applying the dehydration process of the present invention.

As HFA-3W, which may be dealt with as an alternative reaction reagent to hexafluoroacetone, is represented by

[Chemical Formula 1]

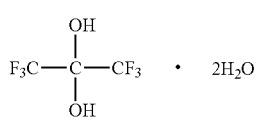   · 2H$_2$O it is a gem-diol dihydrate resulting from a reaction between hexafluoroacetone and water and is a liquid having a boiling point of 106° C. Even if HFA-3W is distilled, it is not possible to release water to obtain hexafluoroacetone.

Furthermore, hexafluoroacetone monohydrate is a compound different from hexafluoroacetone and is represented as gem-diol. An equilibrium of the following formula between hexafluoroacetone and water is established, and the equilibrium shifts extremely rightward.

[Chemical Formula 2]

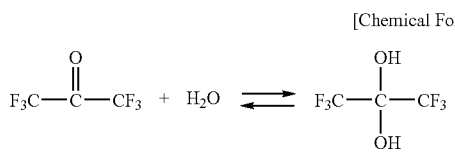

Hexafluoroacetone monohydrate is a solid having a melting point of 52° C., which is high in sublimation property and strong in hygroscopic property. Although it decomposes at 46° C., it is not possible to obtain hexafluoroacetone by distillation, similar to HFA-3W.

On the other hand, a hexafluoroacetone-hydrogen fluoride adduct is a 1:1 adduct of hexafluoroacetone and hydrogen fluoride, represented by heptafluoroisopropanol of the following formula. Heptafluoroisopropanol alone is a thermally unstable compound, and it is considered that there is a partial decomposition into hexafluoroacetone and hydrogen fluoride at a temperature not lower than boiling point (14-16° C.) and that an equilibrium of the following formula is established. The equilibrium depends on temperature, and heptafluoroisopropanol is decomposed by 35% at 20° C. and by 70% at 100° C.

[Chemical Formula 3]

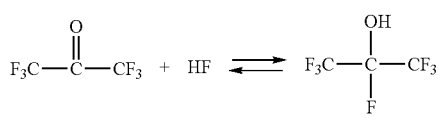

There is a report (U.S. Pat. No. 3,745,093 Patent Publication) that HFA-HF can be separated by distillation under non-equilibrium condition, but it is not possible to separate hexafluoroacetone and hydrogen fluoride even if distillation is conducted by a normal method (French Patent No. 1372549).

In the course of completing the present invention, it has been confirmed by NMR measurement in hydrogen fluoride by the inventors and the like that HFA-HF is heptafluoroisopropanol, and, if an excessive amount of hydrogen fluoride is coexistent, it exists stably as it is heptafluoroisopropanol with no decomposition even if it is left at room temperature or higher.

It is possible to conduct dehydration of a hexafluoroacetone hydrate of the present invention by any type of batch type, half batch type or continuous type by using a common distillation apparatus equipped with a distillation pot, a distillation column, a condenser and other devices As the material of the apparatus, it is possible to use stainless steel, nickel alloy steel, silver, fluororesin, carbon and polyethylene, or metal materials lined or cladded with these materials. For the distillation pot, the distillation column and the packing material, with which a hydrogen fluoride aqueous solution of a relatively high temperature is brought in contact, it is preferable to use silver, resin materials, such as fluororesin and the like, resistant to a hydrogen fluoride aqueous solution, or metal materials lined or cladded with these materials. As the distillation column, it is possible to use any of packing-type formed of a publicly known packing material, a tray column, etc.

The process of the present invention can be conducted under reduced pressure or pressurized condition, specifically even under a condition of a pressure of about 0.05-2 MPa. In the following, the case of conducting it under atmospheric pressure is explained. Conducting it under other pressure conditions also belongs to the scope of the present invention. It is easy for a person skilled in the art to optimize the conditions, based on the following explanation and technical common sense in this technical field.

The batch type dehydration process is explained.
HFA-3W and hydrogen fluoride are introduced into the distillation pot (column bottom) of the distillation column.

Relative to 1 mol of HFA-3W, hydrogen fluoride is necessary by 1 mol or greater, preferably 2-100 mols, more preferably 3-50 mols, still more preferably 5-30. If hydrogen fluoride is too little, the effect of dehydration is insufficient, and operation of the distillation does not become stable. If it is too much, there is no problem in the effect of dehydration. With this, consumption of utility becomes large, and it is accompanied by enlargement of the apparatus. Each of them is not preferable. Here, it suffices that HFA-3W is a hexafluoroacetone hydrate. It may be one having a hydration number less than 3, such as hexafluoroacetone monohydrate. Furthermore, it may be an aqueous solution of a hexafluoroacetone hydrate. As a raw material used for the dehydration, it is preferably HFA-3W or one having a hydration number less than that. As the hydrogen fluoride, anhydrous hydrogen fluoride, which is available for industrial use, is suitable. In principle, however, the water content is not essential. It is possible to use even one containing about 50 mass % of water.

By increasing the column bottom temperature to exceed boiling point of hydrogen fluoride, vapor is liquefied at the column top by the condenser to start reflux. After a certain period of time, it gets closer to 16° C., which is boiling point of HFA-HF. By gradually taking the reflux liquid out, the temperature gets closer to boiling point (19.5° C.) of hydrogen fluoride. While making an adjustment to maintain the reflux condition, the reflux liquid is taken out. In case that the amount of reflux decreases, the column bottom temperature is gradually increased. At the initial stage of the distillation, a component containing a lot of HFA-HF is taken out of the column top at 16-20° C. Then, the temperature of the reflux liquid increases gradually. The HFA-HF content decreases, and a component containing a lot of hydrogen fluoride is taken out. It is necessary to maintain the temperature of the reflux liquid in a range not to greatly exceed boiling point of hydrogen fluoride. Otherwise, dehydration of hydrogen fluoride becomes incomplete, and water is contained in the column top liquid. Although the admissible water content depends on use of the dehydrated HFA, it is 1 mass % or lower, normally 0.01 mass % or lower. Furthermore, the distillation is continued. It can be continued until the column bottom temperature, depending on the composition of hydrogen fluoride and water, increases to 112° C., the azeotropic temperature of hydrogen fluoride aqueous solution. Upon this, the column bottom liquid forms a maximum boiling point azeotrope of 38 mass % hydrogen fluoride and 62 mass % water. The column bottom liquid contains substantially no hexafluoroacetone. The admissible residual HFA depends on the use of the hydrogen fluoride aqueous solution, but is 1 mass % or lower, normally 0.01 mass % or lower. As to the column bottom temperature, it can be conducted until the maximum azeotropic temperature of the hydrogen fluoride aqueous solution. It is also can be conducted at a temperature lower than the maximum azeotropic temperature as long as it is not lower than boiling point (19.5° C.) of hydrogen fluoride. In that case, it results in obtaining a hydrogen fluoride aqueous solution having a concentration determined by boiling point, but the concentration may be determined by the use of the hydrogen fluoride aqueous solution. In this way, a component formed of hexafluoroacetone or HFA-HF and hydrogen fluoride and a component (hydrogen fluoride aqueous solution) formed of hydrogen fluoride and water are separately obtained.

Next, the case of conducting the process of the present invention by a continuous process is explained.

In the above-mentioned batch type dehydration process, it is preferable to conduct a shift to the continuous process from a condition in which the distillation column is maintained in a stable reflux condition. In the continuous process, it is operationally easy to use a hexafluoroacetone hydrate that the compositional ratio of hexafluoroacetone to water is constant, for example, HFA-3W. Therefore, the case of using HFA-3W is explained in the following. In general, it is preferable not to vary the composition ratio of hexafluoroacetone to water, but it is not necessary to be a specific composition ratio (in this case, the molar ratio of water/HFA is 3). HFA-3W and hydrogen fluoride are continuously introduced into the distillation column. HFA-HF and hydrogen fluoride are continuously taken out of the column top, and the hydrogen fluoride aqueous solution out of the column bottom. It is also possible to intermittently conduct the continuous operation of introducing hexafluoroacetone hydrate and hydrogen fluoride, taking HFA-HF and hydrogen fluoride out of the column top, and taking the hydrogen fluoride aqueous solution out of the column bottom.

It is possible to not only introduce a hexafluoroacetone hydrate and hydrogen fluoride into the distillation column through separate pipes, but also introduce them after their previous mixing. It is preferable to have the same positions for the introduction into the distillation column. It is possible to set the position (height) for the introduction into the distillation column at an arbitrary position from the column bottom to the column top. It is, however, preferable to introduce them at the position (height) corresponding to the boiling point of a mixed liquid resulting from the theoretical amounts of water and hydrogen fluoride, which are generated by a dehydration reaction of preferably HFA-3W and hydrogen fluoride.

The reason why dehydration can effectively be conducted in the process of the present invention is assumed that, in the case of mixing hexafluoroacetone trihydrate with one equivalent or more of hydrogen fluoride, a reaction or equilibrium shown in the following formula is established in a short period of time, and in the distillation an equilibrium condition formed of three components of HFA-HF, hydrogen fluoride and an azeotropic composition of water and hydrogen fluoride is established.

[Chemical Formula 4]

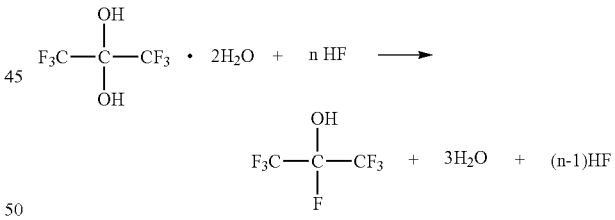

EXAMPLES

In the following, the present invention is explained in detail by examples, but the present invention is not limited to these examples.

Example 1

Batch Type Production Process

As to material of the dehydration apparatus, a fluororesin or polyethylene was used for all of the parts with which hexafluoroacetone, hexafluoroacetone trihydrate and anhydrous hydrogen fluoride are brought into contact. As the distillation pot, a polytetrafluoroethylene container of 10 cm diameter×15 cm height was used. As the distillation column, there was used a PFA column of 3 cm diameter×45 cm height packed by a length of 35 cm with polyethylene Raschig rings (4 mm diameter×4 mm length) as a packing material. As the condenser, there was used a PFA cylindrical container of 10 cm diameter×15 cm height equipped in the inside with a coiled tube to make a refrigerant to flow. As a receiver for an effluent from the column top, a 500 ml PFA container was used.

After putting 220 g of HFA-3W into the distillation pot, it was cooled with a dry ice/acetone bath to solidify it. Then, 240 g of anhydrous hydrogen fluoride was weighed and put thereinto. Under a cooled condition (−20° C.), it was set on the distillation column. It was allowed to stand still as it was until room temperature. Then, heating was started with a water bath and then an oil bath. During this, a conspicuous generation of heat in the distillation pot by the mixing was not observed.

As the heating was continued, reflux was observed at an upper part of the distillation column. Then, temperature of the reflux portion started to become lower than boiling point (19.5° C.) of hydrogen fluoride, and reflux of HFA-HF was confirmed. Upon this, it was started to take the reflux liquid out, while securing reflux to maintain temperature of the column top at around 19.5° C., boiling point of hydrogen fluoride. The reflux liquid (HFA-nHF) taken out was received in the receiver cooled with ice, and the volume was recorded over time. At the time when a suitable amount was collected, the container was changed, followed by measuring the volume and the mass, putting into a storage container made of polyethylene, and storing with sealing in a refrigerator.

Since the column bottom temperature increases with lowering of the hydrogen fluoride concentration at the column bottom portion by the progress of the distillation, the oil bath temperature was adjusted to always have a temperature difference of 20° C. or greater between the column top and the column bottom. Temperature of the column bottom showed on occasions temperature of the gas phase portion of the distillation pot due to decrease of the amount of the interior content (It was the same in the following). Temperatures of the column bottom portion and the distillation column increased gradually, but temperature of the column top was almost constantly maintained at 20° C. to maintain a suitable reflux. At the time when the column bottom temperature showed 60° C., the distillation was stopped.

After the distillation, the reflux liquid (column top effluent) recovered from the column top was 252 g (the molar ratio n of HFA-nHF: 4.3, yield of hexafluoroacetone: 99%), and the column bottom liquid was a hydrogen fluoride aqueous solution (71 mass %) of 188 g. Existence of water was not confirmed by measuring water content of the reflux liquid by Karl Fischer's method. Hexafluoroacetone was not detected in the column bottom liquid.

Example 2

Batch Type Production Process (a) The distillation pot was charged with 181 g of the hydrogen fluoride aqueous solution (71 mass %) recovered from the column bottom after termination of the distillation of Example 1, 220 g of HFA-3W and 344 g of anhydrous hydrogen fluoride. A distillation similar to that of Example 1 was started. While the reflux liquid of the column top was taken out, the distillation was continued until the column bottom temperature showed 51° C. With this, the column top effluent was 249 g (the molar ratio n of HFA-nHF: 4.15, yield of hexafluoroacetone: 99%), and the column bottom liquid was a hydrogen fluoride aqueous solution (76 mass %) of 489 g. Existence of water was not confirmed by measuring water content of the column top effluent by Karl Fischer's method. Hexafluoroacetone was not detected in the column bottom liquid.

(b) After termination of the distillation of (a), the distillation pot was charged with 412 g of the hydrogen fluoride aqueous solution (76 mass %) recovered from the column bottom, and a distillation similar to that of Example 1 was started. While the reflux liquid of the column top was taken out, the distillation was continued until the column bottom temperature showed 85° C. With this, the column top effluent was hydrogen fluoride of 197 g, and the column bottom liquid was a hydrogen fluoride aqueous solution (62 mass %) of 275 g. Existence of water was not confirmed by measuring water content of the column top effluent by Karl Fischer's method. Hexafluoroacetone was not detected in the column bottom liquid.

(c) After termination of the distillation of (b), the distillation pot was charged with 267 g of the hydrogen fluoride aqueous solution (62 mass %) recovered from the column bottom, and a distillation similar to that of Example 1 was started. While the reflux liquid of the column top was taken out, the distillation was continued until the column bottom temperature showed 116° C. With this, the column top effluent was hydrogen fluoride of 54 g, and the column bottom liquid was a hydrogen fluoride aqueous solution (48 mass %) of 206 g. Existence of water was not confirmed by measuring water content of the column top effluent by Karl Fischer's method. Hexafluoroacetone was not detected in the column bottom liquid.

Example 3

Batch Type Production Process

A distillation was conducted by using the same apparatus as that of Example 1. After putting 220 g of HFA-3W into the distillation pot, it was cooled with a dry ice/acetone bath. Then, 122 g of anhydrous hydrogen fluoride was weighed and put thereinto. Under a cooled condition (−20° C.), it was set on the distillation column. Then, similar to Example 1, the distillation was continued until the column bottom temperature showed 121° C. and stopped.

After the distillation, the reflux liquid (column top effluent) recovered from the column top was 229 g (the molar ratio n of HFA-nHF: 3.5, yield of hexafluoroacetone: 99%), and the column bottom liquid was a hydrogen fluoride aqueous solution (46 mass %) of 104 g. Existence of water was not confirmed by measuring water content of the reflux liquid by Karl Fischer's method. Hexafluoroacetone was not detected in the column bottom liquid.

Example 4

Batch Type Production Process

A distillation was conducted by using the same apparatus as that of Example 1. After putting 220 g of HFA-3W into the distillation pot, it was cooled with a dry ice/acetone bath. Then, 271 g of anhydrous hydrogen fluoride was weighed and put thereinto. Under a cooled condition (−20° C.), it was set on the distillation column. Then, the distillation was continued until the column bottom temperature showed 128° C. and stopped.

After the distillation, the reflux liquid (column top effluent) recovered from the column top was 389 g (the molar ratio n of HFA-nHF: 11, yield of hexafluoroacetone: 99%), and the column bottom liquid was a hydrogen fluoride aqueous solution (38 mass %) of 96 g. Existence of water was not confirmed by measuring water content of the reflux liquid by Karl Fischer's method. Hexafluoroacetone was not detected in the column bottom liquid.

Example 5

Continuous Production Process

A metering pump (EH-B10SH-100PR9 made by IWAKI CO., LTD.) as a device for supplying HFA-3W, and a device prepared by combining a needle valve with a cylinder equipped with an inner pipe and a branch pipe, which were made of stainless steel, as a device for supplying hydrogen fluoride were added to the apparatus shown in Example 1, thereby using it as the dehydration apparatus. Flow rate was adjusted by the reading of a weighing scale.

Firstly, a distillation pot was charged with 303 g of a 60 mass % hydrogen fluoride aqueous solution prepared by mixing hydrogen fluoride with water, and the distillation was started. At the time when reflux of hydrogen fluoride was confirmed, 638 g of a mixed liquid (the molar ratio of hydrogen fluoride to HFA-3W: 13) of HFA-3W and hydrogen fluoride was continuously supplied for 5 hours to the position of ¼ of the distillation column height from the column top, and an effluent from the column top was collected in a receiver. During the supply of the mixed liquid, while maintaining the column bottom temperature at about 107° C., the column top temperature was maintained in 16.5° C. to 20.5° C. by adjusting the amount of effluent.

The column top effluent of 567 g recovered from the column top at the time of termination of the dehydration treatment had a molar ratio of hexafluoroacetone/hydrogen fluoride of 10. Existence of water was not confirmed by measuring water content of this effluent from the column top by Karl Fischer's method. The column bottom liquid at the time of termination of the distillation was a hydrogen fluoride aqueous solution (48 mass %) of 370 g. Hexafluoroacetone was not detected in the column bottom liquid. The total recovery percentage (material balance) was not lower than 99.9%, the recovery percentage of hexafluoroacetone was 99.6%, and the recovery percentage of hydrogen fluoride was 100%.

Example 6

Batch Type Production Process

A distillation was conducted by using the same apparatus as that of Example 1. After putting 220 g of HFA-3W into the distillation pot, it was cooled with ice. Then, 271 g of anhydrous hydrogen fluoride was weighed and added to HFA-3W in the distillation pot. Temperature of the mixture increased to about 30° C. by mixing. Then, similar to Example 1, the distillation was continued until the column bottom temperature became 127° C. and stopped.

After the distillation, the reflux liquid (column top effluent) recovered from the column top was 390 g (the number n of HFA-nHF: 11), and the column bottom liquid was a hydrogen fluoride aqueous solution (38 mass %) of 95 g. Existence of water was not detected by measuring water content of the reflux liquid by Karl Fischer's method. HFA was not detected in the column bottom liquid.

Example 7

Batch Type Production Process

A distillation was conducted by using the same apparatus as that of Example 1. At room temperature (about 25° C.) the distillation pot was charged with 358 g of 70 mass % hydrogen fluoride aqueous solution and 430 g of HFA-3W. Then, the reflux liquid was taken out while controlling it so that the column top temperature became 15-16° C. Similar to Example 1, the distillation was continued until the column bottom temperature became 107° C. and stopped.

After the distillation, the reflux liquid (column top effluent) recovered from the column top was 339 g (the number n of HFA-nHF: 1), and the column bottom liquid was a hydrogen fluoride aqueous solution (50 mass %) of 449 g.

INDUSTRIAL APPLICABILITY

The dehydration process of the present invention has an advantage that it generates almost no waste since hydrogen fluoride is used as a dehydration agent. In addition, since anhydride to be obtained is a hydrogen fluoride adduct of hexafluoroacetone, there is a characteristic that it is particularly effective in the case of using hydrogen fluoride as a solvent or the like in reactions.

The invention claimed is:

1. A process for dehydrating a hexafluoroacetone hydrate, comprising:
    introducing a hexafluoroacetone hydrate and hydrogen fluoride either as a mixture or separately into a distillation column; and
    obtaining a composition containing hexafluoroacetone or a hexafluoroacetone-hydrogen fluoride adduct and hydrogen fluoride as a low boiling component.

2. A process according to claim 1, wherein the hexafluoroacetone hydrate and the hydrogen fluoride are continuously introduced either as a mixture or separately into the distillation column.

3. A process according to claim 1, wherein the hexafluoroacetone hydrate is hexafluoroacetone trihydrate.

4. A process according to claim 2, wherein the hexafluoroacetone hydrate is hexafluoroacetone trihydrate.

5. A process according to claim 1, wherein the hexafluoroacetone hydrate is a hexafluoroacetone hydrate containing water.

6. A process according to claim 2, wherein the hexafluoroacetone hydrate is a hexafluoroacetone hydrate containing water.

7. A process according to claim 3, wherein the hexafluoroacetone hydrate is a hexafluoroacetone hydrate containing water.

8. A process for dehydrating a hexafluoroacetone hydrate, comprising:
    introducing a hexafluoroacetone hydrate and hydrogen fluoride either as a mixture or separately into a distillation column;
    obtaining a composition containing hexafluoroacetone or a hexafluoroacetone-hydrogen fluoride adduct and hydrogen fluoride as a low boiling component; and
    obtaining a composition containing water and hydrogen fluoride as a high boiling component.

9. A process according to claim 8, wherein the hexafluoroacetone hydrate and the hydrogen fluoride are continuously introduced either as a mixture or separately into the distillation column.

10. A process according to claim 9, wherein the composition containing water and hydrogen as the high boiling component is continuously obtained from a column bottom portion.

11. A process according to claim 8, wherein the hexafluoroacetone hydrate is hexafluoroacetone trihydrate.

12. A process according to claim 9, wherein the hexafluoroacetone hydrate is hexafluoroacetone trihydrate.

13. A process according to claim 10, wherein the hexafluoroacetone hydrate is hexafluoroacetone trihydrate.

14. A process according to claim 8, wherein the hexafluoroacetone hydrate is a hexafluoroacetone hydrate containing water.

15. A process according to claim 9, wherein the hexafluoroacetone hydrate is a hexafluoroacetone hydrate containing water.

16. A process according to claim 10, wherein the hexafluoroacetone hydrate is a hexafluoroacetone hydrate containing water.

17. A process according to claim 11, wherein the hexafluoroacetone hydrate is a hexafluoroacetone hydrate containing water.

18. A process according to claim 12, wherein the hexafluoroacetone hydrate is a hexafluoroacetone hydrate containing water.

19. A process according to claim 13, wherein the hexafluoroacetone hydrate is a hexafluoroacetone hydrate containing water.

\* \* \* \* \*